United States Patent  
Nikander et al.

(10) Patent No.: US 9,956,359 B2
(45) Date of Patent: May 1, 2018

(54) METHOD AND APPARATUS COMPRISING STEPPED MOUTHPIECE FOR AEROSOL DRUG DELIVERY

(75) Inventors: Kurt Nerner Nikander, Salem, MA (US); Dirk Von Hollen, Clark, NJ (US); John S. Viviano, Ontario (CA); Eugene Nelson Scarberry, Trafford, PA (US); Ian Thomas Petherbridge, West Sussex (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 978 days.

(21) Appl. No.: 13/131,947

(22) PCT Filed: Nov. 23, 2009

(86) PCT No.: PCT/IB2009/055297
§ 371 (c)(1),
(2), (4) Date: May 31, 2011

(87) PCT Pub. No.: WO2010/073148
PCT Pub. Date: Jul. 1, 2010

(65) Prior Publication Data
US 2011/0240015 A1  Oct. 6, 2011

Related U.S. Application Data

(60) Provisional application No. 61/140,138, filed on Dec. 23, 2008.

(51) Int. Cl.
*A61M 11/00* (2006.01)
*A61M 15/00* (2006.01)

(52) U.S. Cl.
CPC ........ *A61M 15/00* (2013.01); *A61M 15/0021* (2014.02); *A61M 11/005* (2013.01);
(Continued)

(58) Field of Classification Search
CPC ............... A61M 15/055; A61M 15/00; A61M 15/0028; A61M 15/033; A61M 15/0043;
(Continued)

(56) References Cited

U.S. PATENT DOCUMENTS 5,645,423 A  7/1997 Collins, Jr.
5,645,424 A  7/1997 Collins, Jr.
(Continued)

FOREIGN PATENT DOCUMENTS

CN  101554504 A  10/2009
JP  2006026436 A  2/2006
WO  WO9622802 A1  8/1996

OTHER PUBLICATIONS

John S. Viviano: "Acoustic Reflection: Review and Clinical Applications for Sleep-Disordered Breathing", vol. 6 No. 3, 2002, pp. 129-149.
(Continued)

Primary Examiner — Todd J Scherbel
Assistant Examiner — Ned T Heffner
(74) Attorney, Agent, or Firm — Michael W. Haas

(57) ABSTRACT

The invention of the present application relates to an apparatus to aid in administering inhaled pharmaceutical aerosol to a patient. The apparatus is used in conjunction with an aerosol delivery device. The apparatus comprises steps on the top and bottom of the apparatus, which when used aid the patient causes mandibular advancement, and opening of the mouth, causing opening of patient's airway, resulting in improved aerosol lung deposition. The invention also relates to a method of using such apparatus in a combination with an aerosol delivery device or a system, and to the mouthpiece of said apparatus.

23 Claims, 10 Drawing Sheets

(52) U.S. Cl.
CPC ..... *A61M 15/009* (2013.01); *A61M 2202/064* (2013.01); *A61M 2206/11* (2013.01)

(58) Field of Classification Search
CPC .......... A61M 15/0045; A61M 15/0051; A61M 15/0065; A61M 15/0048; A61M 2202/064; A61M 15/0033–15/0041
USPC ............. 128/202.21, 200.11–200.16, 203.12, 128/203.15, 203.23, 203.24, 204.13, 848, 128/849, 857–862, 200.24, 200.26, 128/201.26, 206.29, 207.14; 131/270–273
See application file for complete search history.

(56) References Cited

U.S. PATENT DOCUMENTS

| | | | |
|---|---|---|---|
| 5,794,627 A | 8/1998 | Frantz et al. | |
| 6,604,527 B1 | 8/2003 | Palmisano | |
| 6,631,721 B1 | 10/2003 | Salter et al. | |
| 6,857,427 B2* | 2/2005 | Ziegler et al. | 128/200.23 |
| 6,877,513 B2 | 4/2005 | Scarberry | |
| 6,904,908 B2* | 6/2005 | Bruce et al. | 128/200.23 |
| 6,966,319 B2* | 11/2005 | Fitton | 128/848 |
| 7,137,393 B2 | 11/2006 | Pivovarov | |
| 7,178,529 B2 | 2/2007 | Kownacki | |
| 7,311,103 B2 | 12/2007 | Jeppesen | |
| 7,331,349 B2 | 2/2008 | Brady et al. | |
| 7,451,760 B2 | 11/2008 | Denyer | |
| 7,464,706 B2 | 12/2008 | Steiner | |
| 2007/0039614 A1 | 2/2007 | Djupesland | |
| 2007/0292819 A1* | 12/2007 | Scarberry | A61F 5/566 433/140 |
| 2008/0053437 A1 | 3/2008 | Steiner et al. | |

OTHER PUBLICATIONS

John S. Viviano: "Assessing Orthotic Normalization of Pharyngeal Dynamics", Jul. 2004, vol. 22, No. 3, The Journal of Craniomandibular Practice. pp. 192-208.

Simon McGuire: "Thei-Neb Adaptice Aerosol Delivery (AAD) System—A Holistic Approach to Inhaled Drug Delivery Including Regulatory Approval", Drug Delivery Report Spring/Summer 2006, pp. 29-32.

Ta-Chun Lin et al; "Mouthpiece Diameter Affecs Deposition Efficiency in Cast Models of the Human Oral Airways", Journal of Aerosol Medicine, vol. 14, No. 3, 2001, Mary Ann Liebert, Inc. pp. 335-341.

John S. Viviano: "Airway Orthotics: Normalizing the Pathological Airway", The Journal for Sleep Specialists, vol. 3, No. 1, Jan. 2002.

Kenneth Monahan et al; "Oropharyngeal Dimensions in Adults: Effect of Ethnicity, Gender, Sleep Apnea", Journal of Cliiical Sleep Medicine, vol. 1, No. 3, 2005, pp. 257-263.

Cooke, M. E. et al., "A Thermoplastic Mandibular Advancement Device for the Management of Non-Apnoeic Snoring: a Randomized Controlled Trial", European Journal of Orthodontics, 2006, vol. 28, pp. 327 to 338.

Nikander, K et al., "Adaptive Aerosol Delivery (AAD®) Technology", Journal Expert Opinion on Drug Delivery, vol. 1, Issue 1, 2004, pp. 165-176.

Henke, K. et al., "An Oral Elastic Mandibular Advancement Device for Obstructive Sleep Apnea", American Journal of Respiratory and Critical Care Medicine. 2000, vol. 161, pp. 420 to 425.

* cited by examiner

METHOD AND APPARATUS COMPRISING STEPPED MOUTHPIECE FOR AEROSOL DRUG DELIVERY

This patent application claims the priority benefit under 35 U.S.C. § 119(e) of U.S. Provisional Application No. 61/140,138 filed on Dec. 23, 2008, the contents of which are herein incorporated by reference.

The invention of the present application relates to an apparatus to aid in administering inhaled pharmaceutical aerosol to a patient. The invention also relates to a method of using such apparatus in a combination with an aerosol delivery device or a system.

Medical devices used to deliver drugs in an aerosol form to patients have been used since the mid 1950s. Such devices are used to deliver inhaled pharmaceutical aerosols (IPAs) into lungs of patients. The most common use of such devices is in the treatment of asthma and chronic obstructive pulmonary diseases, in forms of meter dose inhalers, dry powder inhalers, or nebulizers.

A perennial problem with the use of inhalers is the low efficiency of the delivery of the aerosol to its target. In cases of patient administered meter dose inhalers (MDI) or dry powder inhalers (DPI), up to 50% of the aerosolized drug may not reach the lungs of the patient. Various different ways of trying to improve lung deposition have been attempted. Methods to improve lung deposition include patient education, for example, teaching patients about optimal positioning of the inhaler mouthpieces, coordinating of actuation of an inhalers with inhalation, ensuring the patient lips make an effective seal around the mouthpiece of the inhaler, ensuring that the patient places their teeth around the mouthpiece to prevent deposition on the teeth. Other methods include the use of a spacer placed between an inhaler mouthpiece and the mouth of a patient, and redesigning of mouthpieces of inhalers so as to reduce drug deposition on the mouthpieces.

It is known in the art, that the diameter of an intraoral apparatuses has an effect on the inhaled pharmaceutical aerosol deposition in the lungs. To meet this function such intraoral apparatuses are primarily plain oval or tubular designs of sufficient length to pass through the teeth. See T. A. Chun Lin et al., Mouthpiece Diameter Affects Deposition Efficiency in Cast Models of the Human Oral Airways, *J. Aerosol Medicine* 2001, Vol. 14, No. 3, pp 335 to 341. This, and other similar studies, show a trend that larger the cross section of the apparatus, greater the deposition of inhaled pharmaceutical aerosol in the lungs. Although such studies demonstrate that opening of a patient's jaw improves lung deposition, no published studies investigate the effect of any other position of the jaw on inhaled pharmaceutical aerosol lung deposition.

In the art of treatment of snoring and sleep apnea, it is well known that an advancement of a patient's jaw forward may alleviate the patient's symptoms. U.S. Pat. No. 7,331,349 to Brady et al. provides for a method of treating snoring or sleep apnea by advancing the mandible by the use of an extra-oral device. U.S. Pat. No. 7,311,103 to Jeppesen provides for a method of treating Obstructive Sleep Apnea Syndrome utilizing positive airway pressure by creating a single-piece, dual arch airway orthotic, using said orthotic to obturate the oral cavity via an acrylic seal between the upper and lower dental arches. U.S. Pat. No. 6,604,527 to Palmisano and U.S. Pat. No. 5,794,627 to Frantz provide for methods of advancing mandibles by a device that fits over the patient's teeth. U.S. Pat. Nos. 5,645,423 and 5,645,424, both to Collins, disclose orthodontic appliances comprising a set of pivotable segments that may be affixed to opposing upper and lower teeth on one side of patient's dental arch to cause mandible advancement.

However, up to now, no device that advances the mandible for the purposes of improving the delivery of inhaled pharmaceutical aerosol into the patient's lungs has been disclosed or proposed.

Accordingly, it is an object of the present invention to provide an apparatus to aid aerosol delivery to a patient. More specifically, the present invention is directed to such apparatus which comprises a front end, a back end, a top side, a bottom side, a bore through the apparatus from the front end to the back end, an upper step on the top side facing to the back end; and a lower step on the bottom side facing to the front end, wherein the upper step is further towards the back end than is the lower step. The position of the two steps to each other is defined as the step offset.

In one of the embodiments of the apparatus, the front end of the apparatus comprises an inlet port. Such an inlet port may be adapted to attach to an inhaled pharmaceutical aerosol delivery device. The inhaled pharmaceutical aerosol delivery device may be an inhaler.

The object of the present invention is also to provide for the dimensions of the step offset. In one preferred embodiment of the present invention the step offset has a value between −3 mm and +6 mm. In another preferred embodiment of the present invention the step offset is a non-negative value. In a more preferred embodiment, the step offset has a positive value. In a still more preferred embodiment, the step offset is between +3 and +6 mm.

Another object of the present invention is to provide for an apparatus to aid aerosol delivery to a patient comprising a front end, and a back end, a bore through the apparatus from the front end to the back end, wherein the apparatus is further adapted to receive lower and upper teeth of a patient, such that upon insertion of the back end of the tube into the patient's mouth and biting down on the tube causes mandibular advancement. This mandibular advancement opens the upper airway of the patient, which in turn improves the laminar flow of inhaled pharmaceutical aerosol through the airway, hence increasing lung deposition of inhaled pharmaceutical aerosol.

Yet another object of the present invention is to provide for a mouthpiece. A mouthpiece is a part of any device, which is introduced into a patient's mouth. The mouthpiece of the present invention comprises a back end, a top side, a bottom side, an upper step on the top side, a lower step on the bottom side. The upper step faces backwards, and the lower step faces forwards. The upper step is further towards the back end than is the lower step. The mouthpiece may be attached to an aerosol delivery device, such as an inhaler.

It is yet another object of the present invention to provide an inhaled pharmaceutical aerosol delivery device which further comprises a stepped mouthpiece. One of the embodiments of the present invention is a metered dose inhaler comprising a stepped mouthpiece. Another embodiment of the present invention is a dry powder inhaler comprising a stepped mouthpiece. Yet another embodiments of the present invention is a nebulizer comprising a stepped mouthpiece.

It is still another object of the present invention to provide a method of aiding aerosol delivery that does not suffer from the disadvantages associated common method of delivering inhaled pharmaceutical aerosol. This method includes the use of a mandibular advancement apparatus. In one embodiment of the present invention, such apparatus has bore there-through, through which an inhaled pharmaceutical aerosol is introduced to a patient's airway. The advantage of using said method is higher lung deposition of inhaled pharmaceutical aerosols. In one embodiment of the method, the mandibular advancement apparatus comprises an upper step on the top side of the apparatus facing to the back end and a lower step on the bottom side facing away from the back end.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
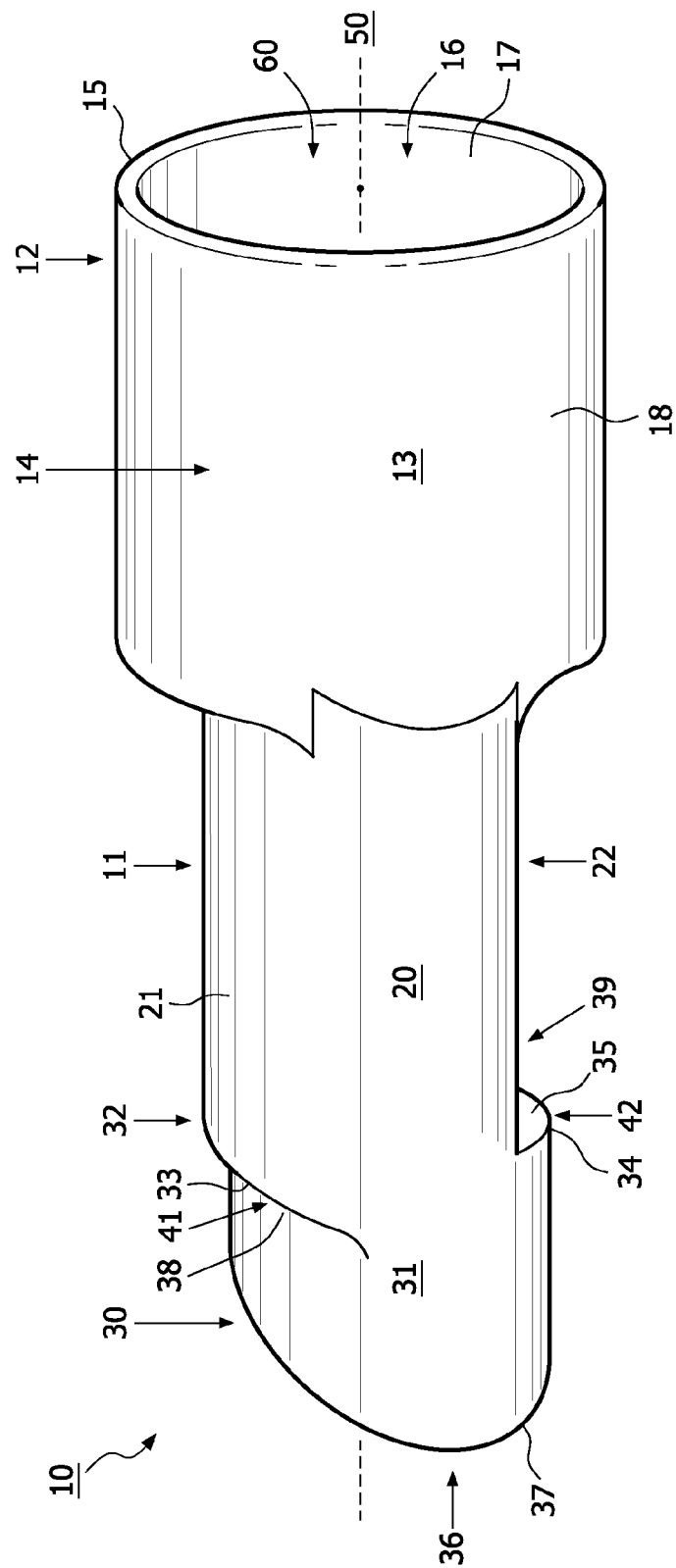
FIG. 1 is a right perspective view of an embodiment of an apparatus of the present invention.

The apparatus of the present invention comprises a mouthpiece of such configuration, that when a patient uses the apparatus properly, the mouthpiece will force the patient's lower jaw into a position to increase the deposition of inhaled pharmaceutical aerosol into the patient's lung. The apparatus of the present invention increases the deposition of the inhaled pharmaceutical aerosol in the patient's lungs by improving the geometry of the oral cavity of the patient to cause a laminar flow of an air/inhaled pharmaceutical aerosol mixture. Positioning the patient's jaw and related anatomical structure in an appropriate way will decrease the deposition of inhaled pharmaceutical aerosol particle in the upper airway, and increase the deposition in the lungs.

FIGS. 1 to 5 illustrate an exemplary embodiment of an apparatus 10 according to one embodiment of the present invention. Apparatus 10 comprises a hollow body 11 with a front end 12, and back end 30 with an imaginary axis 50 leading through hollow body 11. Apparatus 10 comprises a shaft 20 with a mouthpiece 31 on back end 30, and an inlet port 13 at front end 12. Apparatus 10 also comprises a bore 60 through the apparatus from front end 12 to the back end 30. Bore terminates on front end 12 with inlet aperture 16, and on back end 30 with outlet aperture 36.

Apparatus 10 comprises a unitary body which may be formed from a suitable material. Suitable materials may be any biocompatible material, which is acceptable for a safe and effective use by a patient or a medical professional. Any commonly used material in the art of inhaled pharmaceutical aerosols delivery may be used. The material should also provide a relatively rigid structure to the mouthpiece so that a patient does not deform the mouthpiece during the use thereof. A suitable material may be a thermoset plastic, such as acrylonitrile butadiene styrene, poly(methyl methacrylate), polyacrylate, polyethylene, polypropylene, polybutylene, polysulfone, polyphthalamide, polystyrene, polyurethane, polyvinyl chloride, styrene acrylonitrile resin, or copolymers thereof. In a preferred embodiment the suitable material is polyethylene, polypropylene, polyurethane or polycarbonate. In a more preferred the suitable material is polyethylene, or polypropylene.

Apparatus 10 may be formed by any means in the art used to form mouthpieces of medical devices. In the preferred embodiment the mouthpiece is formed by reaction injection molding.

Figure 2:
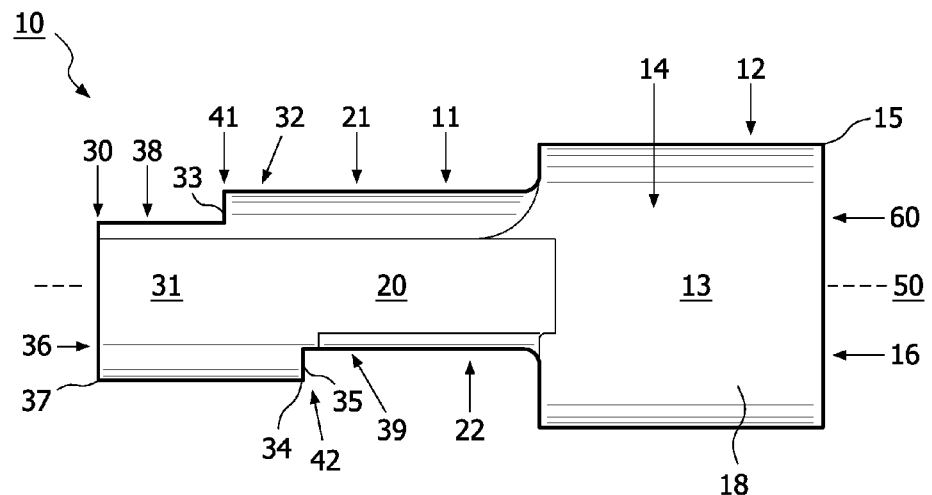
FIG. 2 is a side elevation view of an embodiment of an apparatus of the present invention.
Figure 3:
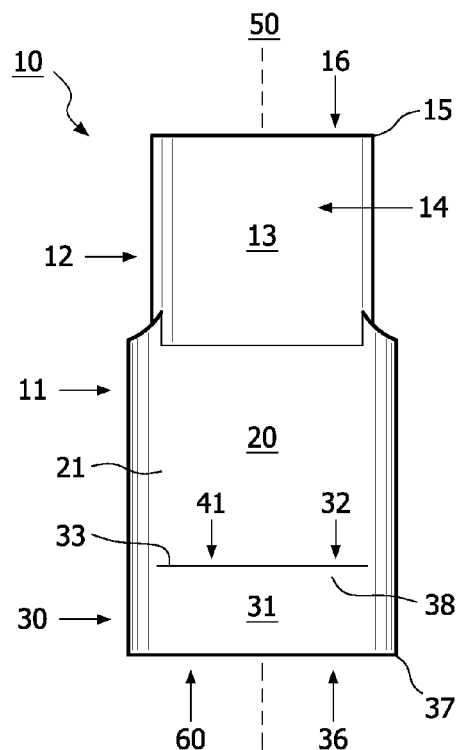
FIG. 3 is a top view of an embodiment of an apparatus of the present invention.
Figure 4:
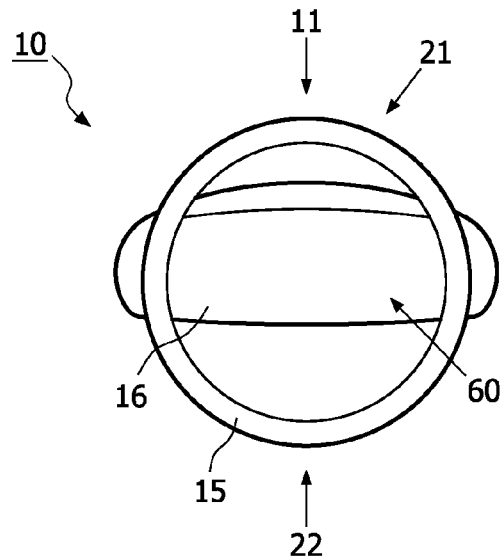
FIG. 4 is a front view of an embodiment of an apparatus of the present invention, looking from the front of the apparatus.
Figure 5A:
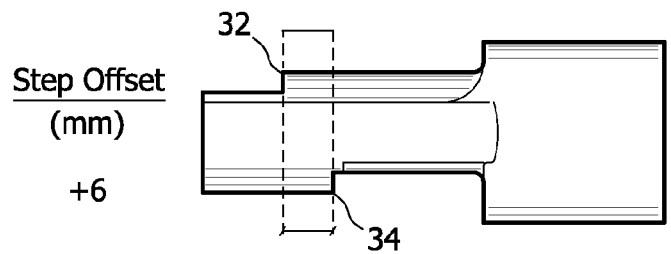
FIG. 5 is a side elevation view of four different embodiments of an apparatus of the present invention, showing various step offset values.
Figure 5B:
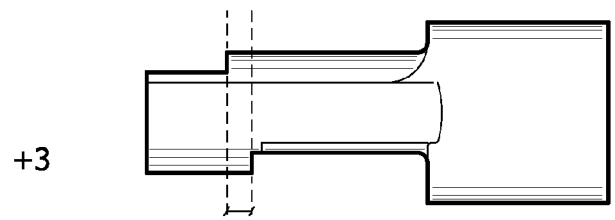
Figure 5C:
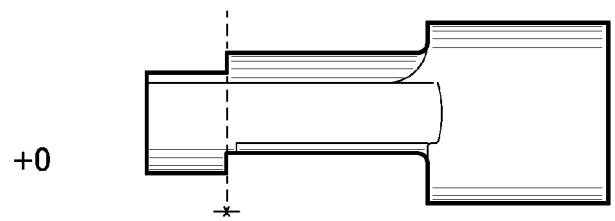
Figure 5D:
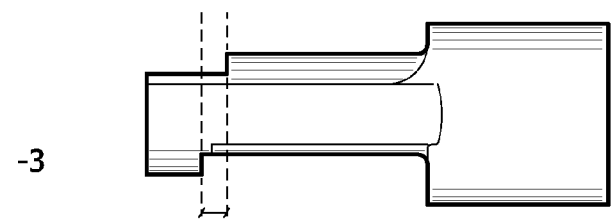

In the embodiment illustrated in FIGS. 1 to 3, apparatus 10 is a unitary body. In an alternative embodiment the apparatus is assembled from a plurality of structural elements forming the parts of apparatus 10. The individual elements may be formed by molding or otherwise forming independently from one another and are subsequently bonded together to form apparatus 10. Such bonding may be permanent, or alternatively, the individual elements may be friction fitted together and may be readily disassembled for easier cleaning of the apparatus.

The apparatus is generally rigid in nature. It is necessary that apparatus 10 be rigid, so that apparatus 10 does not deform during the use of apparatus 10. Specifically, when a patient bites on mouthpiece 31, the mouthpiece does not constrict the inner cross-section of shaft 20. Further, inlet port 13 should also be rigid as to readily accept an exhaust outlet from an inhaler or a spacer.

Inlet port 13 functions as a receiving inlet for inhaled pharmaceutical aerosols or medical gases through an inlet aperture 16. In a preferred embodiment, inlet port 13 is defined by a cylindrical projecting wall 14 defining an interior volume. The interior of the inlet port is fluidly connected to the interior of shaft 20.

In the preferred embodiment the projecting wall surrounding the interior volume has a shape of a right circular cylinder. In an alternative embodiment the projecting wall surrounding the interior volume of the inlet port has a frustal conical shape with the wall slightly angled inward, as to allow for an easier mating with an outlet port of an inhaler device. In another alternative embodiment, the projecting wall surrounding the interior volume of the inlet port has a frustal conical shape with the wall slightly angled outward to allow for an alternative mating with an outlet port of an inhaler device. In yet another embodiment the projecting wall surrounding the interior volume of the inlet port has a general right cylinder shape; examples of general right cylinder shape includes an elliptic cylinder.

Projecting wall 14 terminates on front end 12 with a peripheral edge 15. In a preferred embodiment peripheral edge 15 is generally smooth with slightly rounded corners to ensure that a patient or a medical professional does not cut themselves on the corners, and to aid in mating of an outlet port of an inhaler to the inlet port. In an alternative embodiment the peripheral edge has sharp corners.

During the use of the apparatus, the inlet port 13 is mated with an outlet port of an inhaled pharmaceutical aerosol delivery device (not shown in FIGS. 1 through 5). An inhaled pharmaceutical aerosol delivery device is a device which either generates stored inhaled pharmaceutical aerosol upon actuation to deliver inhaled pharmaceutical aerosol out of an outlet port, or alternatively, is a device through which inhaled pharmaceutical aerosol flows through to an outlet port. Examples of inhaled pharmaceutical aerosol delivery device includes an inhaler (commonly referred to as a puffer), and a spacer. Examples of an inhaler include metered dose inhalers (MDI), dry powder inhalers (DPI), or a nebulizer. Examples of nebulizers include pneumatic nebulizers, ultrasonic nebulizers, and mesh nebulizers. An inhaled pharmaceutical aerosol delivery device also includes devices that deliver condensation aerosols and electrohydrodynamic aerosols.

The apparatus embodiment of the present invention is designed to be used in concert with a metered dose inhaler. Common metered dose inhalers include, but are not limited to, those sold under the tradenames Airomir™, Ventolin®, Atrovent®, Becloforte®, Benclovent®, Berotec®, Combivent®, Flovent®, Tilade®, Serevent®, Intal®, Vanceril®, and QVAR®.

The apparatus of the present invention is also designed to be used with a spacer. A spacer device is designed to make the use of an inhaler much more effective and easier. Also known as an asthma spacer, it is an empty chamber with an inlet port and an outlet port. The use of such spacer devices partially mitigates the difficulty of coordinating the timing of the inhaler actuation and the patient's inhalation. Furthermore, the use of such spacer devices slows down the speed of delivery of the pharmaceutical aerosol into the mouth so that lower percentage of the pharmaceutical aerosol deposits in the oropharynx. Typically, a spacer device has a chamber that fits on the mouthpiece of the inhaler, a mouthpiece of the spacer is placed between patient's lips. The pharmaceutical aerosol is sprayed directly into the chamber of the spacer instead of the patient's mouth. The pharmaceutical aerosol is then inhaled with a slow deep breath.

A spacer may be commercially obtained, or it may be homemade. Spacer devices available to asthma patients include, but are not limited to, ACE® Spacer (DHD Healthcare, Wampsville, N.Y., USA), Aerochamber® (Forest Pharmaceuticals, St Louis, Mo., USA), Easivent Spacer, EZ-Spacer® (WE Pharmaceuticals, Ramona, Calif., USA), Inspirease® (Key Pharmaceuticals, Kenilworth, N.J., USA), AirLife™ Medispacer® (Allegiance Healthcare Corporation, McGaw Park, Ill., USA); LiteAire® (Thayer Medical, Tucson, Ariz., USA), Optichamber® Advantage Valved Holding Chamber (Respironics HealthScan Asthma and Allergy Products, Cedar Grove, N.J., USA), Nebuhaler® (AstraZeneca, UK), VentaHaler Spacer Device, RiteFlo Spacer™, Volumatic®, Babyhaler®, and Nebuchamber®.

The invention of the present application can be used with any device that delivers inhaled pharmaceutical aerosol. The phrase "inhaled pharmaceutical aerosol" refers to any type of medicament that is formulated to be delivered to a patient in aerosolized form into the patient's lungs. As used herein, the term "aerosol" refers to a suspension of solid, solution or liquid particles in a gas. The term "aerosol" also refers to a suspension of a mixture of solid and liquid particles in a gas. The term "aerosol" also refers to liquid particles in a gas, wherein the liquid is a mixture of at least two liquids. Such a mixture can be a homogenous liquid (such as a solution), or it can be a heterogeneous liquid (such as a suspension).

The apparatus of the present invention is designed to work with any aerosol of any common particle size. In a preferred embodiment the mean aerosol particle size is 0.1 to 10 micrometers. In a more preferred embodiment, the mean aerosol particle size is 0.5 to 5 micrometers. In another embodiment of the present invention the aerosol particle size is submicron size. An example of particles with submicron size are nanoparticles.

The mating of the inlet port with an outlet port of an inhaled pharmaceutical aerosol delivery device can be achieved in several ways. In a preferred embodiment an outlet port of the inhaled pharmaceutical aerosol delivery device is friction fitted through inlet aperture 16 into inlet port 13 of apparatus 10. In this embodiment an outer surface of the outlet port is in contact with the inner surface 17 of projecting wall 14.

In the embodiment illustrated in FIGS. 1 to 5, inner surface 17 of projecting wall 14 is smooth. Such smoothness aids in the mechanism of friction fitting. In an alternative embodiment, inner surface 17 has geometric features which help to retain the outlet port of the inhaled pharmaceutical aerosol delivery device so it is matched to the corresponding features on the outlet port of the inhaled pharmaceutical aerosol delivery device. Such geometric features include ridges and other protruding features, and valleys and other intruding features. Such geometric features on the inner surface 17 in such embodiment are coordinated to the matching features on the outer surface of the outer port of inhaled pharmaceutical aerosol delivery device.

In an alternative embodiment the outlet port of the inhaled pharmaceutical aerosol delivery device fits over inlet port 13; namely, outer surface 18 of projecting wall 14 is in contact with the inner surface of the wall of the outlet port of the inhaled pharmaceutical aerosol delivery device. In an alternative embodiment, outer surface 18 has geometric features which help to retain the outlet port of the inhaled pharmaceutical aerosol delivery device by matching to the corresponding feature on the outlet port of the inhaled pharmaceutical aerosol delivery device. Such geometric features include ridges and other protruding features, and valleys and other intruding features. Such geometric features on the outer surface 18 in such embodiment are coordinated to the matching features on the inner surface of the outer port of inhaled pharmaceutical aerosol delivery device.

Shaft 20 is attached on one end to inlet port 13, and terminates on the other end with a mouthpiece 31. Shaft 20 is hollow and is in fluid contact with inlet port 13. The cross-section of the shaft can be of any two dimensional shape, so long as that it of sufficient size for a mouthpiece to fit into a patient's mouth to deliver the inhaled pharmaceutical aerosol. In the embodiment shown in FIGS. 1 to 5, shaft 20 has an elliptic cross-section. In this embodiment the minor axis of the ellipse that defines the cross-section of the shaft is in the vertical direction, and the major axis of the ellipse that defines the cross-section of the shaft is in the horizontal direction. In other preferred embodiments, the cross-section of the shaft may be circular, ellipsoidal, oval, square, square with rounded corners, square with four curvilinear edges, rectangular, rectangular with rounded edges, rectangular with two curvilinear edges, or rectangular with four curvilinear edges, among others. The area of the cross section of bore 60 at narrowest point of bore 60 is defined as the cross section. Such cross section is measured in mm². The size of cross section area in the apparatus of the present invention may be between 50 and 500 mm², preferably between 100 and 300 mm².

During use, the apparatus needs to be positioned between the upper and lower teeth of the patient. It is beneficial that the patient takes the apparatus into his/her mouth and introduces the inhaled pharmaceutical aerosol into the inlet port as for the inhaled pharmaceutical aerosol to flow through the device into the mouthpiece, into the patient's oral cavity, and finally into the patient's lungs. To achieve proper orientation of the apparatus by the patient, in a preferred embodiment markings on the apparatus are oriented towards the patient. Furthermore, in a preferred embodiment, only the inlet port 13 is capable of mating with an outlet port of an inhaled pharmaceutical aerosol delivery device and not mouthpiece 31 of the apparatus 10.

In the embodiment illustrated in FIGS. 1 to 4, shaft 20 has a top side 21 and a bottom side 22. Both top side 21 and bottom side 22 stretch from a border between shaft 20 and inlet port 13, to peripheral edge 37 of mouthpiece 31. In order to use the apparatus properly, the apparatus 10 needs to be positioned between the upper and lower teeth of the patient properly. It is beneficial that the patient places top side 21 of shaft 20 with contact with his/her top teeth, and bottom side 22 of shaft 20 with his/her bottom teeth. Placing the apparatus 10 into the patients mouth upside down would likely result in sub-optimal lung deposition of inhaled pharmaceutical aerosol. In a preferred embodiment top side 21 is marked to indicate to the user of the apparatus the axial orientation of apparatus 10. Such markings may be in form of writing, symbols, or juvenile drawings, although any suitable indicia may be used.

Shaft 20 terminates on back end 30 with mouthpiece 31. Mouthpiece 31 is the portion of shaft 20 which is introduced into the oral cavity of the patient. Mouthpiece 31 also comprises outlet aperture 36, through which inhaled pharmaceutical aerosol is introduced into the oral cavity of a patient.

In the embodiments illustrated by FIGS. 1 to 5, mouthpiece 31 comprises upper step 32, and lower step 34. Upper step 32 is a step on top side 21 of shaft 20. Upper step 32 faces towards back end 30 of apparatus 10, meaning that looking from back end 30 towards front end 12, riser 33 of upper step 32 is visible. Lower step 34 is a step on bottom side 22 of shaft 20. Lower step 34 faces forward (towards front end 12), meaning that looking along the bottom side 22 from front end 12 towards back end 30, riser 35 of lower step 34 is visible.

Mouthpiece 31 further comprises an area 38 where the patient's upper teeth are placed, and an area 39 where the patient's lower are placed. The upper front teeth are placed so that the upper front teeth of the patient are contacted with top side 21 and the apparatus is manipulated so that the front of the upper front teeth are pushed against upper riser 33. In a preferred embodiment of the invention, the incisal surfaces of the maxillary central incisors connect with area 38, while at the same time the facial surfaces (also referred to as the buccal surfaces) of the maxillary central incisors connect with riser 33. In an alternative embodiment at least one of the incisal surfaces of at least one of the maxillary lateral incisor also connect with area 38. In another alternative embodiment at least one of the facial surfaces of at least one the maxillary lateral incisors also connect with riser 33. In yet another embodiment the incisal surface of at least one of the maxillary lateral incisors connects with area 38, while at the same time the facial surface of at least one the maxillary lateral incisors also connect with riser 33.

The lower front teeth of the patient are placed so that the lower front teeth are in contact with the lower side 22, and the apparatus is manipulated so that the back of the lower front teeth are pushed against lower riser 35. In a preferred embodiment of the invention, the incisal surfaces of at least one of the mandibular central incisors or mandibular lateral incisors connect with area 39, while at the same time at least one of the lingual surfaces of the mandibular central incisors or mandibular lateral incisors connect with lower riser 35. Any combination of simultaneous connections of incisal surfaces of mandibular incisors with area 39 and connections of lingual surfaces of mandibular incisors with lower riser 35 are satisfactory for the purposes of the present invention.

The term "contact" of a tooth surface with a surface of the apparatus 10 does not necessarily mean a full or a complete matching of the tooth surface with a portion of the surface of the apparatus. It is sufficient if only a small portion, such as a single point, of the tooth surface contacts a small portion of the surface of the apparatus 10. Upper riser 33 also includes edge 41 of upper step 32. Similarly, lower riser 35 also includes edge 42 of lower step 34. Thus, in one embodiment the facial surface of a maxillary incisor can contact upper riser 33 only on edge 41 of upper step 32. In another embodiment, the lingual surface of a mandibular incisor can contact lower riser 35 on edge 42 of lower step 34.

The relative position of upper step 32 to lower step 34 on apparatus 10, is an important feature of the presently described invention. Step offset, measured in millimeters, is the distance along the axis 50, between the position of the upper step 32 relative to the lower step 34. As illustrated in FIGS. 5(*a*) to 5(*d*), different values of step offset of the mouthpiece are possible. Step offset value of 0 mm, as illustrated in FIG. 5(*c*), means that upper step 32 is aligned with lower step 34. A positive offset value, such as in FIGS. 5(*a*) and 5(*b*) indicates that upper step 32 is further back along axis 50 (i.e., closer to back end 30 of mouthpiece 31) than is lower step 34.

The phrase "further back" or "further towards the back end" indicates the position of the steps relative to each other with respect to the axis 50 passing through the center of the apparatus 10. The position of the intersection of an imaginary right angle projection line from the axis 50 of the apparatus 10 to the center of one step is compared to the position of the intersection of an imaginary right angle projection line from the axis 50 of the apparatus 10 to the center of the other step. The step of which the intersection of the projection line is further back along the axis of the apparatus is considered to be further back, or further towards the back end 30 of the apparatus 10.

The stepped mouthpiece may also be incorporated into the structure of an inhaled pharmaceutical aerosol delivery device. Under one embodiment the inhaled pharmaceutical aerosol delivery device comprising the stepped mouthpiece is a metered dose inhaler. A metered dose inhaler comprises at least two components: a canister, and an actuator. The canister contains a drug which is to be delivered to patient's lungs, a liquified gas propellant, and other excipients, such as a stabilizer. The canister also comprises a metering dose valve with an actuating stem. The actuator comprises a discharge nozzle which mates with the actuating stem. The patient using the inhaler presses down on the top of the canister, while supporting the lower portion of the actuator. Actuation of the device releases a single metered dose of liquid propellant that contains the drug. A breakup of the volatile propellant into droplets, followed by rapid evaporation of the droplets yields micron-sized particles aerosol particles containing the drug.

The peripheral edge of the mouthpiece of the present invention can have any shape appropriate to define the outlet aperture. Under a preferred embodiment the shape of the outlet aperture is convex. The outlet aperture can have a shape of a circle, an ellipse, an oval, a square, a square with rounded corners, a square with four curvilinear edges, a rectangle, a rectangle with rounded edges, a rectangle with two curvilinear edges, a rectangle with four curvilinear edges, or other similar shapes.

Figure 11:
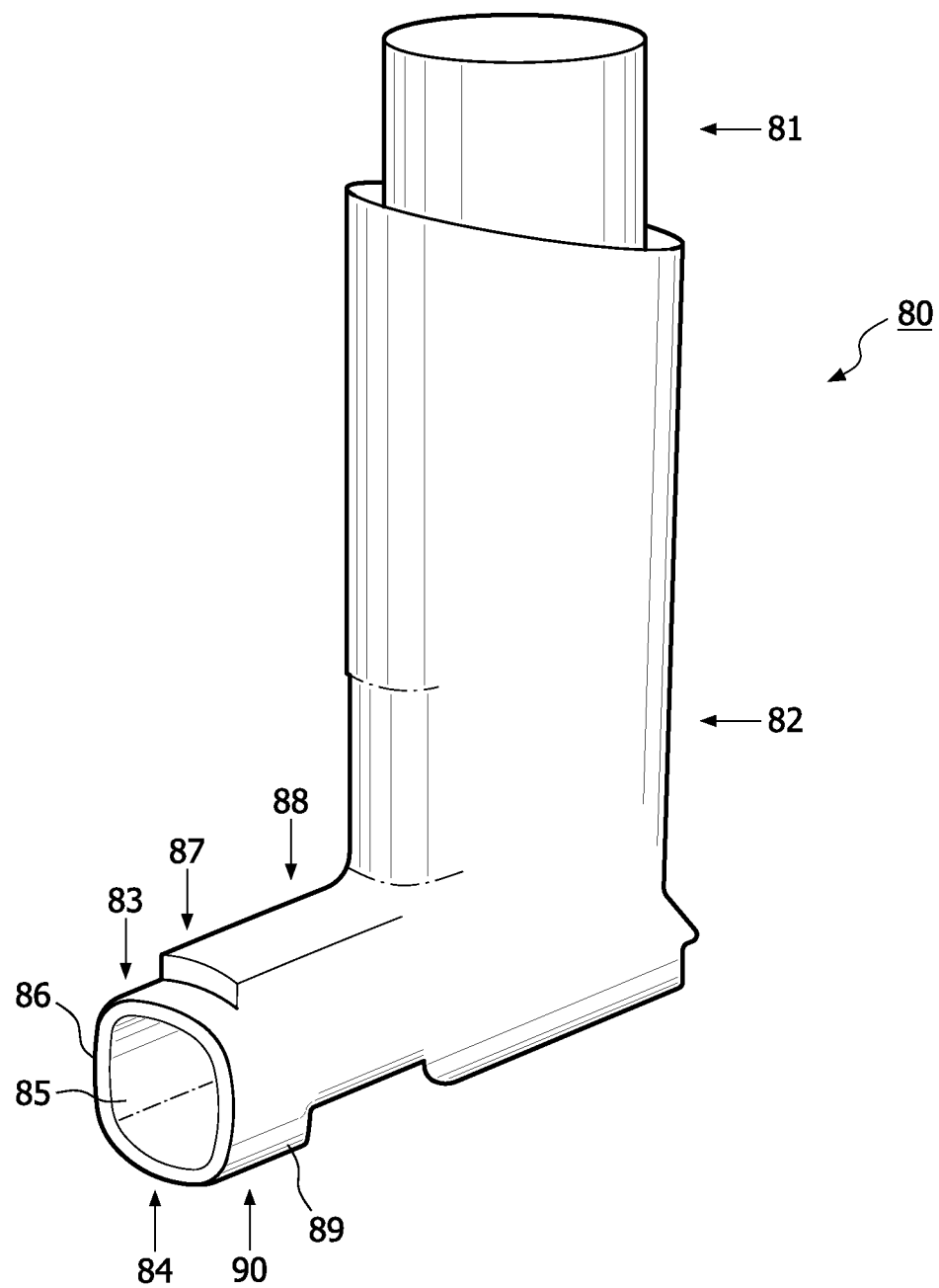
FIG. 11 shows a perspective view of an embodiment of the present invention comprising a metered dose inhaler with a stepped mouthpiece.

An embodiment of a metered dose inhaler comprising the mouthpiece is illustrated in FIG. 11. Metered dose inhaler 80 comprises canister 81, and actuator 82. The actuator comprises mouthpiece 83, which at back end 84, contains outlet aperture 85, defined by peripheral edge 86. The mouthpiece further comprises an upper step 87 on upper side 88 of mouthpiece 83, and lower step 89 on lower side 90 of mouthpiece 83. The exemplary embodiment in FIG. 11 shows the shape of aperture 85 defined by peripheral edge 86 as a square with four curvilinear edges.

In another embodiment of the present invention the stepped mouthpiece is incorporated into the structure of a dry powder inhaler. Any dry powder inhaler in which a patient places a mouthpiece of the dry powder inhaler between the patient's teeth is may be adapted to incorporate the stepped mouthpiece. A dry powder inhaler may be a single-dose device, or a multiple-dose device. Examples of dry powder inhalers include Aerolizer®, HandiHaler™, Flexhaler®, Diskus®, and Twisthaler®.

Figure 12A:
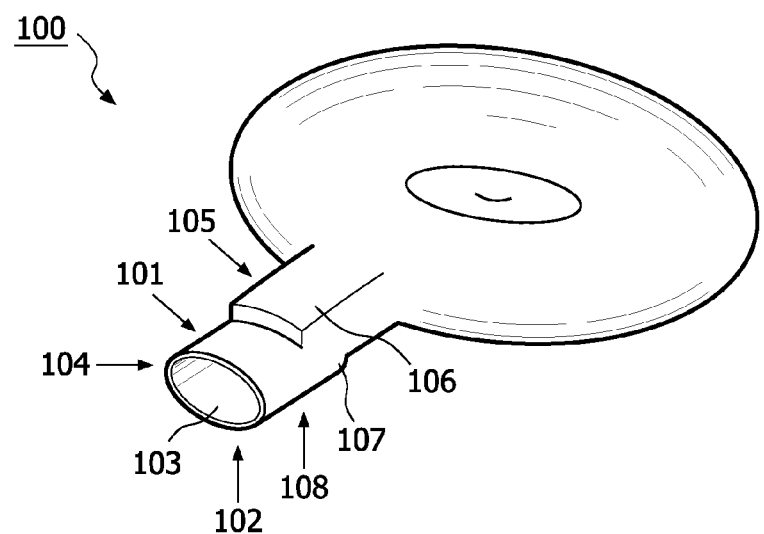
FIG. 12(a) shows a perspective view of an embodiment of the present invention comprising a dry powder inhaler with a stepped mouthpiece.

An embodiment of a dry powder inhaler comprising a stepped mouthpiece is illustrated in FIG. 12(a). Dry powder inhaler 100 comprises mouthpiece 101, which at back end 102, contains outlet aperture 103, defined by peripheral edge 104. The mouthpiece further comprises an upper step 105 on upper side 106 of mouthpiece 101, and lower step 107 on lower side 108 of mouthpiece 101. The exemplary embodiment in FIG. 12(a) shows the shape of aperture 103 defined by peripheral edge 104 as a circle.

In yet another embodiment of the present invention the stepped mouthpiece is incorporated into the structure of a nebulizer. Any nebulizer in which a patient places a mouthpiece of the nebulizer between the patient's teeth is may be adapted to incorporate the stepped mouthpiece. Examples of nebulizers of the present invention which comprise stepped mouthpieces include pneumatic nebulizers, ultrasonic nebulizers, and mesh nebulizers. Nebulizers of the present invention which comprise stepped mouthpieces also include devices that deliver condensation aerosols and electrohydrodynamic aerosols.

Figure 12B:
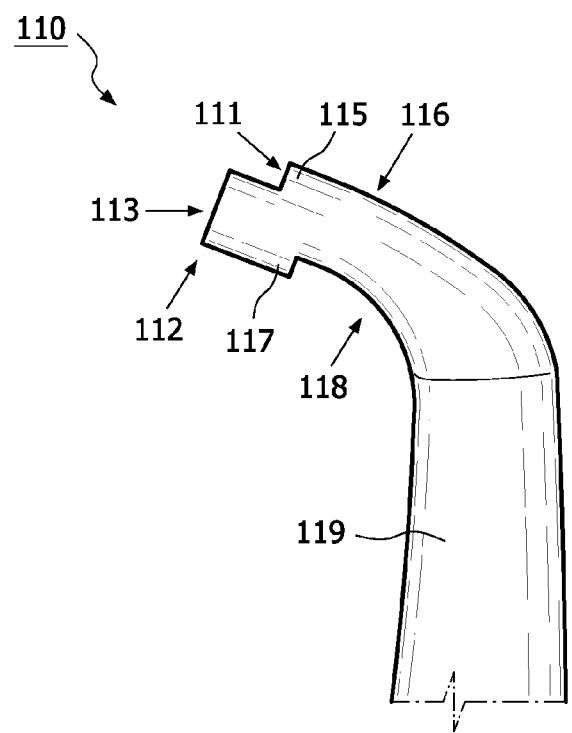
FIG. 12(b) shows a side elevation view of an embodiment of the present invention comprising a portion of a nebulizer with a stepped mouthpiece.

An embodiment of a nebulizer comprising a stepped mouthpiece is illustrated partially in FIG. 12(b). Nebulizer outlet tube 110 comprises mouthpiece 111, which at back end 112, contains outlet aperture 113. The mouthpiece further comprises an upper step 115 on upper side 116 of mouthpiece 111, and lower step 117 on lower side 118 of mouthpiece 111. Nebulizer outlet tuber 110 is connected to the rest of the nebulizer by tubing 119.

Referencing FIGS. 1 to 4, the mechanics of the use the mouthpiece of the present invention, as incorporated into any of the above embodiments, and its effect on the mandibular advancement, is described as follows. The combination of placement of upper front teeth on area 38 and against upper riser 33, while at the same time placing the lower front teeth on area 39 and against lower riser 35, may have the effect of pushing the jaw unnaturally forward. The natural position of teeth in most patients is that the upper front teeth fit slightly over the lower front teeth. Even with a step offset value of 0 mm, the lower teeth are advanced forward compared to the upper teeth. As illustrated in the experimental section below, an increase in the amount of mandibular advancement generally correlates to an increase in the volume of the oral cavity. Offset of +2 to +6 mm is judged to significantly improve the volume of the oral cavity, and thus the increase of lung deposition.

The optimal offset varies with each patient. For some patients the optimal step offset may be +2 mm, with others, it may be +5 mm. Although in cases of patients suffering from mandibular prognathism apparatuses with step offsets of +12 mm may be used, typically the upper practical limit of step offset is about +7 mm. For an average person step offset values above +6 mm are considered painful, lowering the likelihood of patient's compliance with a dosing regiment. In one preferred embodiment of the present invention the step offset has a value between −3 mm and +6 mm. In another preferred embodiment of the present invention the step offset is a non-negative value. In a more preferred embodiment, the step offset has a positive value. In a still more preferred embodiment, the step offset is between +3 and +6 mm.

It is important to note that the mandibular advancement is patient dependent, and that an optimal value of mandibular advancement in order to maximize inhaled pharmaceutical aerosol lung deposition may be found anywhere along the mandibular advancement axis, ranging between no advancement and maximum advancement. Advancing the mandible too much or not enough may constrict the oropharyngeal cross-section.

In some patients, the optimal mandibular advancement may be achieved by using a mouthpiece where the step offset is negative. The negative offset may be used, for example, by a patient suffering from a case of mandibular prognathism wherein the mandible is naturally advanced so as to constrict the oropharyngeal cross-section. There are at least two reasons why mandibular advancement in absolute terms is greater than the step offset. Firstly, a step offset of 0 mm means that the steps are lined up; however, using a mouthpiece comprising a 0 mm mouthpiece actually advances the lower teeth over the upper teeth. Specifically, in order for an apparatus with a 0 mm step offset position to fit a patient's teeth properly, the lingual surfaces of mandibular incisors line up with facial surfaces of maxillary incisors, thus in effect the mandibular incisors appear to be advanced compared to the maxillary incisors. Secondly, in most patients, in the natural position of the jaw, the maxillary incisors overlap mandibular incisors; hence the jaw must advance in order for the incisors to even line up with each other, and advance even more for the lingual surfaces of mandibular incisors line up with facial surfaces of maxillary incisors.

Another important parameter for construction of a mouthpiece of the invention is the cross-section area of the mouthpiece. In one embodiment of the invention the cross section has an elliptical shape, with an axis in the horizontal plane, and an axis in the vertical plane. In some embodiments of the mouthpiece of the present invention with elliptical cross-section the horizontal axis may be larger than the vertical axis. In other embodiments of the mouthpiece of the present invention with elliptical cross-section the horizontal axis may be smaller than the vertical axis. The horizontal axis may be any length which may be practicable; in preferred embodiments the length of the horizontal axis is between 15 and 30 mm. The vertical axis may be any length which may be practicable; in preferred embodiments the length of the vertical axis is between 0 and 40 mm.

Figure 6:
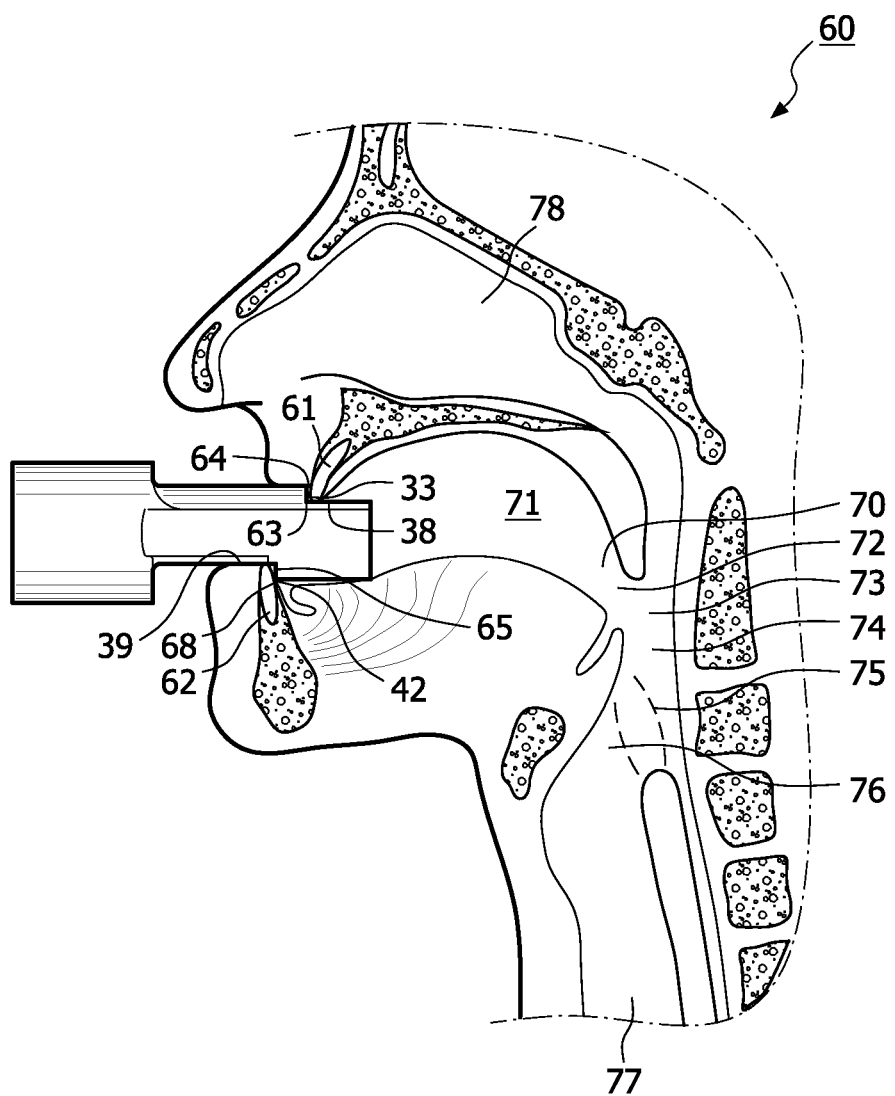
FIG. 6 shows a use of an apparatus of the present invention by a patient.

When a patient uses the apparatus, the patient pushes the upper front teeth against the upper step, and pulls the lower teeth against the lower step of the mouthpiece. This opens up the upper airway to deliver the inhaled pharmaceutical aerosol into patient's lungs. A patient is a person to whom it is desired that an inhaled pharmaceutical aerosols be delivered; the definition of the term "patient" includes both a sick person as well as a healthy person. FIG. 6 illustrates a typical use of the apparatus with a positive offset as used by a patient. Apparatus 10 held by patient 60, clamped down between the patient's maxillary incisors 61, and mandibular incisors 62. FIG. 6 shows one embodiment of the use, namely, incisal surface 63 of maxillary incisor 61 connects with area 38, facial surface 64 of maxillary incisor 61 connects with upper riser 33, incisal surface 65 of mandibular incisor 62 connects with area 39, and lingual surface 68 connects with edge 42.

FIG. 6 also shows the geography of the airway 70 which is used to deliver the inhaled pharmaceutical aerosol to the lungs. Airway 70 comprises oral cavity 71, oropharyngeal junction 72, oropharynx 73, epiglottis 74, hypopharynx 75, glottis 76, and larynx 77. Because the nasal cavity is not directly involved in the delivery of inhaled pharmaceutical aerosol to the lungs, for the purposes of the description of the present invention, nasal cavity 78 is omitted from the definition of airway 70.

One of the advantage of the stepped mouthpiece in any of the embodiments discussed herein is that the use of such a device results in combined opening and advancement of the jaw. This combined opening and advancement of the jaw not only opens the airway, but also causes an appropriate positioning of the patient's tongue. Unlike in traditional mouthpieces, in which the patient's tongue tends to block the flight of the aerosol by either blocking the mouthpiece with the tip of the tongue or blocking partially the airway with an arch of the bulk of the tongue muscle, the combined horizontal and vertical movement of a patient's jaw resulting in the use of the mouthpiece of the present invention appears to eliminate the problem of the tongue arch and leaves the tip of the tongue free.

The apparatus of the present invention, and the mouthpiece of the present invention, are a result of scientific studies into methods of improving inhaled pharmaceutical aerosol lung deposition. Lung scintigraphy studies using different breathing maneuvers to control parameters such as inhalation cross-sectional area, time and flow rate were performed. However, even with the most effective inhalation maneuver oropharyngeal deposition in the range 15 to 35% was observed. Oropharyngeal deposition is not desired, because any deposition in oropharynx means poorer deposition of the inhaled pharmaceutical aerosol in lungs.

It is postulated that the deposition of inhaled pharmaceutical aerosols in lungs is improved by changing the geometry of the upper airway of the patients. As described below, the geometry of upper airway as measured by an acoustic pharyngometer of test subjects showed measurable improvement with devices that enlarged the mouth opening and that advanced the mandible of a patient.

The geography of the upper airway may be measured by an acoustic pharyngometer. Through acoustic reflection technology, an acoustic pharyngometer affords the ability to objectively evaluate and document the pharyngeal airway. This physiological tool comprises of a wavetube housing a loudspeaker, two microphones recording the resulting incident and reflected sound waves, and a computer to record and interpret the resulting data. See J. S. Viviano, Assessing Orthotic Normalization of Pharyngeal Dynamics, *J. Craniomandibular Practice* July 2004, vol. 22, no. 3, pp 192 to 208. A pharyngogram, an output of the pharyngometer, shows graphically the geometry of the pharyngeal airway. Specifically, the pharyngogram represents a cross-sectional area of the airway from the oral cavity caudal to the glottis. The area under the curve represents the volume over a given length of airway, and landmarks along the pharyngogram relate to specific anatomical landmarks.

The use of acoustic pharyngometer to investigate inhaled pharmaceutical aerosol deposition in the lungs is novel. Traditionally, the use of acoustic pharyngometer has been confined to investigation of sleep apnea or snoring. See, for example, K. Monahan et al., Oropharyngeal Dimensions in Adults: Effect of Ethnicity, Gender, and Sleep Apnea, *J. Clin. Sleep Medicine* 2005, vol. 1, no. 3, pp 257 to 263; and J. S. Viviano, Acoustic Reflection: Review and Clinical Applications for Sleep Disordered Breathing, *Sleep and Breathing* 2002, vol. 6, No. 3, 2002. Furthermore, traditionally the data from the acoustic pharyngometer has been obtained during the exhalation portion of subjects' breaths; in the experiment to measure the geography of patient airway for the purposes of investigating inhaled pharmaceutical aerosol lung deposition, the data was collected during the inhalation portion of subjects' breaths.

The results of the experiment show several important trend which demonstrate that an apparatus comprising stepped mouthpiece will aid in deposition of inhaled pharmaceutical aerosol in a patient's lungs. Firstly, the cross section of the oral cavity increases with larger step offset. Secondly, it was surprising and unexpected that the cross section of hypopharynx increased with an increasing step offset. Thirdly, it was surprising and unexpected that the total volume of the airway increases with increasing step offset. Fourthly, it was surprising and unexpected that for patients suffering from sleep apnea the use of the device resulted in sizable increase of hypopharynx.

Such increases in cross sections of the part of the airways, or increases to the total volume of the airway are important to the delivery of inhaled pharmaceutical aerosol to patient's lungs.

EXPERIMENTAL

Twelve different apparatuses with three different cross section areas and four different step offset values were formed. The three cross-sectional areas of the apparatus were 161 $mm^2$ (the area of an ellipse with the minor axis laying in the vertical direction and measuring 10 mm, and the major axis laying in the horizontal direction and measuring 28 mm), 232 $mm^2$, (15 mm×28 mm) and 278 $mm^2$ (20 mm×28 mm). The four step offsets were −3 mm, 0 mm, +3 mm and +6 mm.

Pharyngograms of four different patients for each of the twelve apparatuses was obtained. Data was obtained at approximately 0.42 cm intervals. Four runs were made for each patient for each apparatus.

Figure 7:
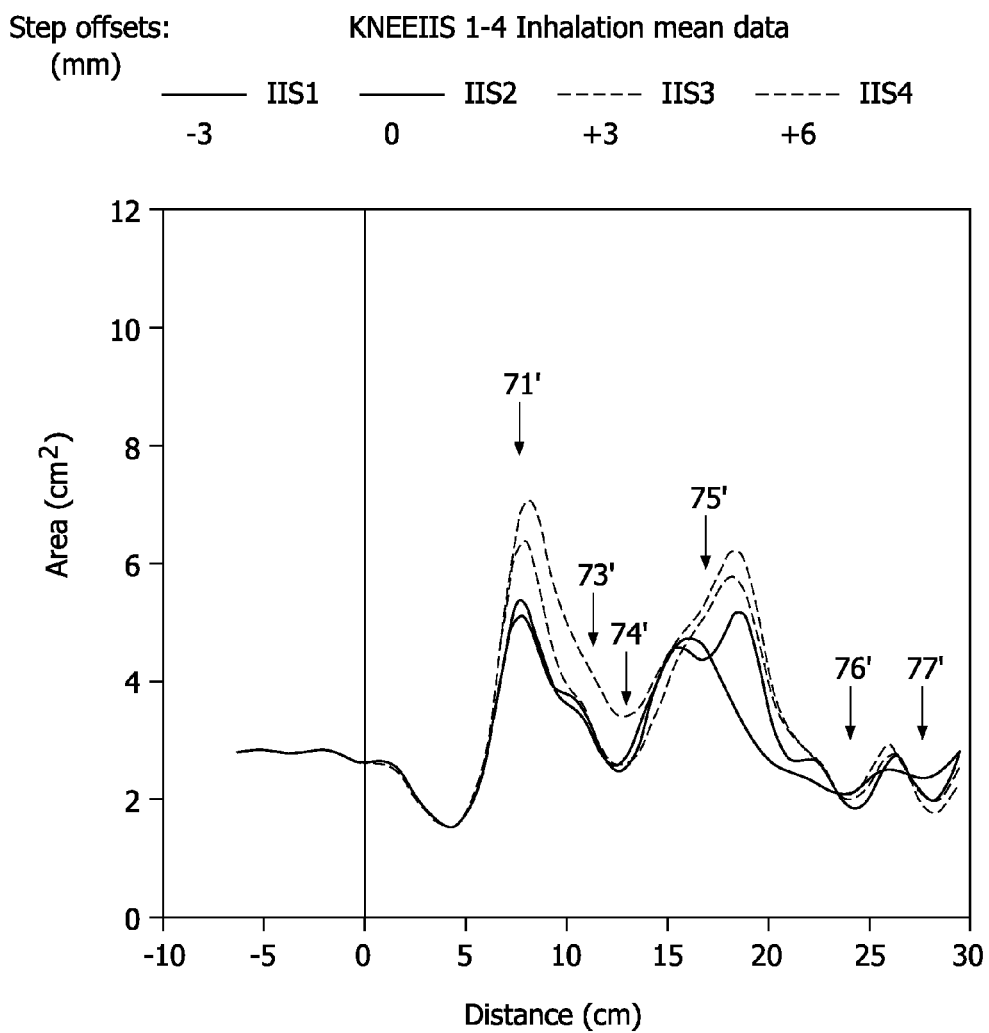
FIG. 7 shows four pharyngograms of four apparatuses with the same small cross section and with differing step offsets for a typical patient.
Figure 8:
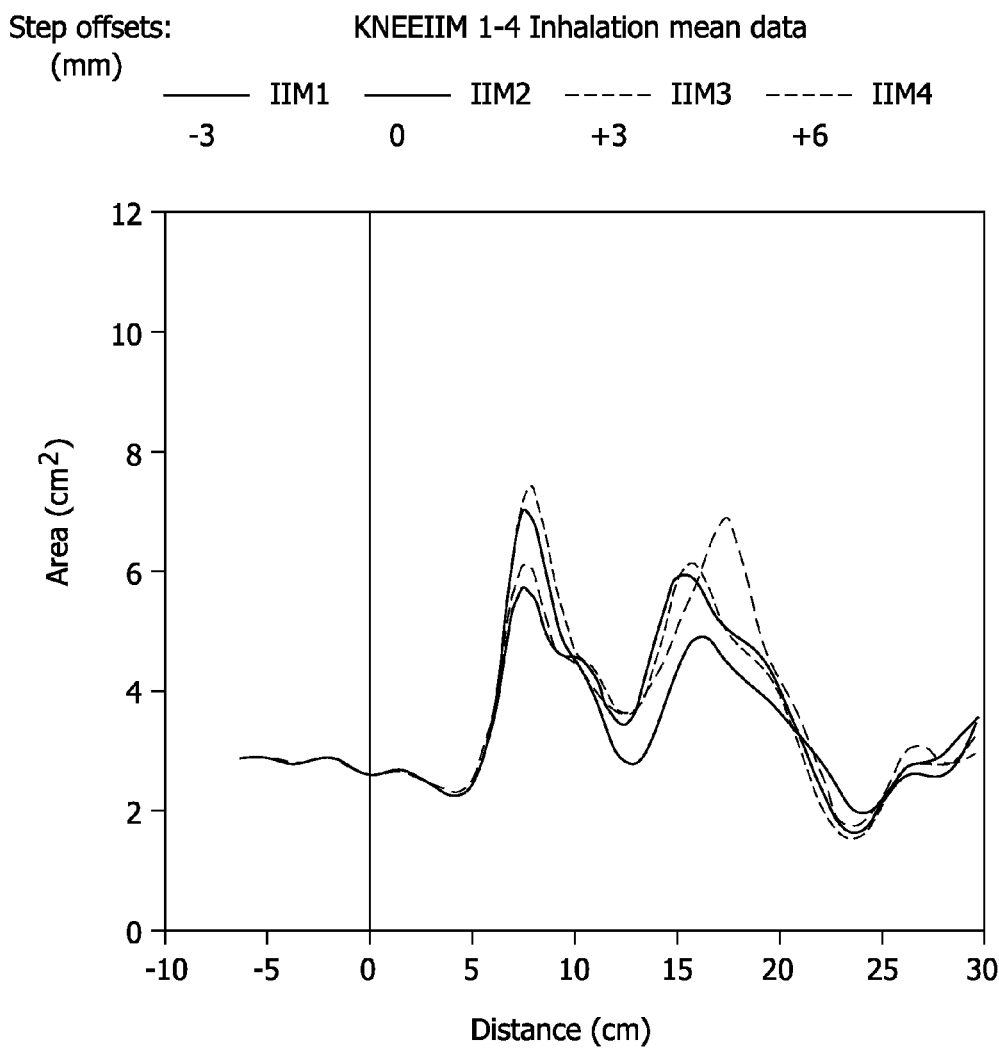
FIG. 8 shows four pharyngograms of four apparatuses with the same medium sized cross section and with differing step offsets for a typical patient.
Figure 9:
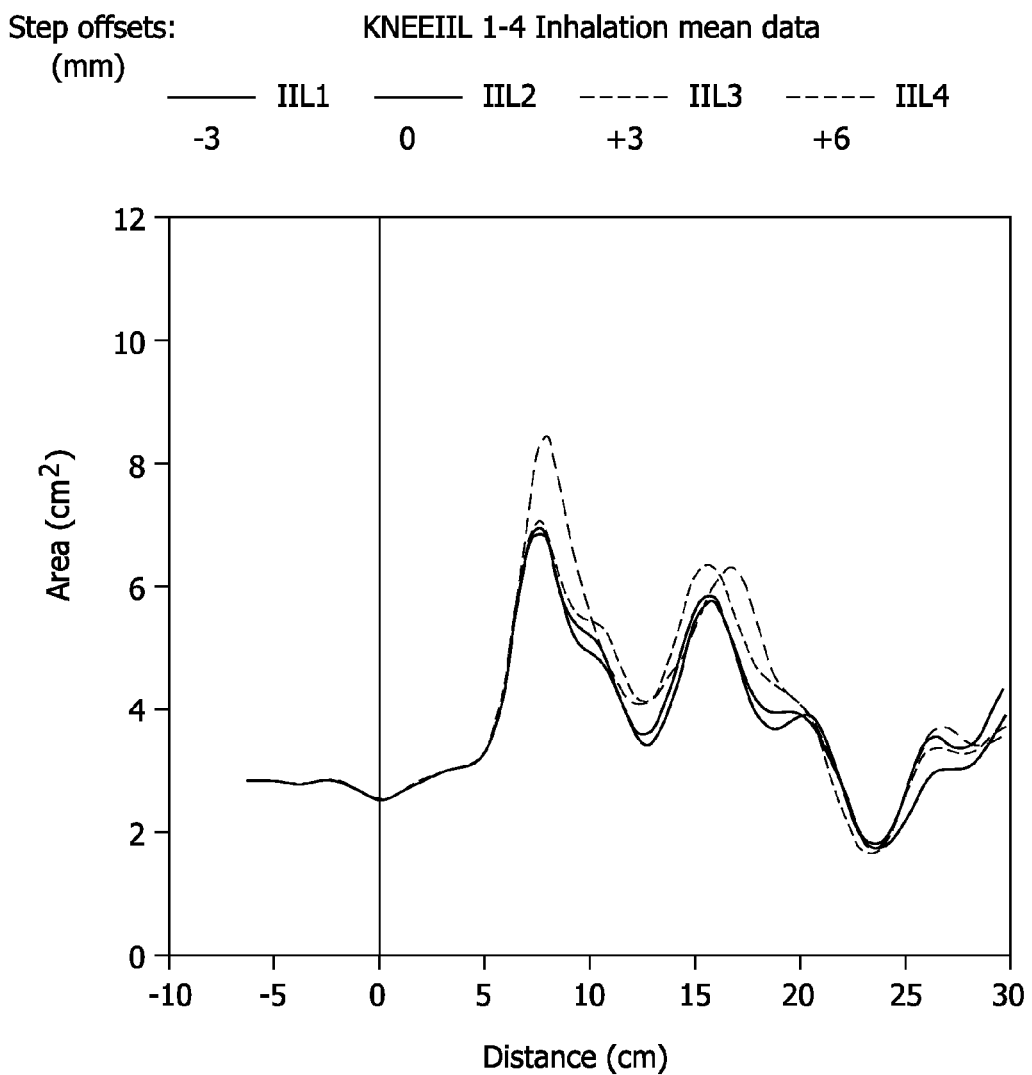
FIG. 9 shows four pharyngograms of four apparatuses with the same large cross section and with differing step offsets for a typical patient.

Typical pharyngograms are presented in FIGS. 7 to 9. FIG. 7 show four curves representing four different step offsets for apparatuses with 161 $mm^2$ cross section for a typical patient. FIG. 8 show four curves representing four different step offsets for apparatuses with 232 $mm^2$ cross section for the same patient. FIG. 9 show four curves representing four different step offsets for apparatuses with 278 mm² cross section for the same patient.

The peaks and valleys of the curves in FIG. 7 are indicative of the geography of the patient's airway. The distance along the vertical axis represents the distance along the air pathway measured in cm from the patient's teeth. The first large peak, labeled 71', corresponds to the patient's oral cavity, shoulder 73' corresponds to the oropharynx, valley 74' corresponds to the epiglottis, large peak 75' corresponds to the hypopharynx, valley 76' corresponds to the glottis, and features 77' correspond to the features in larynx.

FIG. 7 shows that with increasing step offset not only does the oral cavity open, but surprisingly, the cross section of hypopharynx increases. This is also observed in FIGS. 8 and 9. These graphs thus demonstrate that show that the cross section of the oral cavity increases with larger step offset. Furthermore, the cross section of hypopharynx increased with an increasing step offset. The increase of the hypopharynx cross section with increase step offset is an unexpected result.

The volume of an airway was calculated based on the pharyngographical data, and is presented in Table 1. For each patient, Table 1 lists the volume of his airway in cm³. The columns indicate the cross sectional area of the apparatus. The rows indicate the step offset in mm.

TABLE 1

| | | Cross section of the apparatus | | |
| --- | --- | --- | --- | --- |
| | | Small (161 mm²) | Medium (232 mm²) | Large (278 mm²) |
| Patient 1 | | | | |
| Step offset | −3 mm | 107.0 | 118.5 | 128.4 |
| | 0 mm | 110.2 | 122.9 | 131.6 |
| | +3 mm | 115.9 | 122.4 | 135.7 |
| | +6 mm | 124.2 | 130.4 | 140.1 |
| Patient 2 | | | | |
| Step offset | −3 mm | 98.4 | 113.6 | 122.4 |
| | 0 mm | 98.0 | 110.9 | 121.7 |
| | +3 mm | 109.5 | 117.0 | 121.3 |
| | +6 mm | 108.2 | 116.6 | 124.7 |
| Patient 3 | | | | |
| Step offset | −3 mm | 141.7 | 130.3 | 135.5 |
| | 0 mm | 135.3 | 136.7 | 137.4 |
| | +3 mm | 135.2 | 156.5 | 142.2 |
| | +6 mm | 143.1 | 157.6 | 165.3 |
| Patient 4 | | | | |
| Step offset | −3 mm | 106.1 | 118.2 | 124.6 |
| | 0 mm | 115.3 | 124.1 | 132.3 |
| | +3 mm | 114.1 | 121.2 | 136.0 |
| | +6 mm | 129.0 | 130.8 | 133.1 |

For each of the subjects, the greater the cross-section of the apparatus, the greater the volume of the airway for a particular offset. However, it is surprising and unexpected that the total volume of the airway also generally increases with increasing step offset for each of the patients.

In some patients, the data shows that greater the opening of the mouth, greater the opening of the airway. However, it is surprising to note that based on the data obtained from the pharyngograms, in some patients opening of the mouth too much restricts the airflow through the pinch points, such as the oropharyngeal junction or epiglottis. Based on this surprising data, it is envisioned that the optimal lung deposition occurs somewhere between the two extreme positions, namely, the optimal lung deposition with respect to the vertical position of the jaw occurs when the mouth is opened partially.

Furthermore, in some patients, the data shows that greater the mandibular advancement, greater the opening of the airway. However, it is also surprising to note that based on the data obtained from the pharyngograms, in some patients advancing the mandible too much restricts the airflow through the pinch points, such as the oropharyngeal junction or epiglottis. Based on this surprising data, it is envisioned that the optimal lung deposition occurs somewhere between the two extreme positions, namely, the optimal lung deposition with respect to horizontal position of the jaw occurs when the jaw is advanced only part way.

It is thus surprising that the horizontal position, the vertical positioning, or a combination of the horizontal and vertical positioning of the jaw dictates the optimal lung deposition. Plotting of inhaled pharmaceutical aerosol lung deposition response vs. advancement of the jaw and opening of the jaw results in a mound-shaped response surface. It has been determined that the position of the mound is patient variable.

Figure 10:
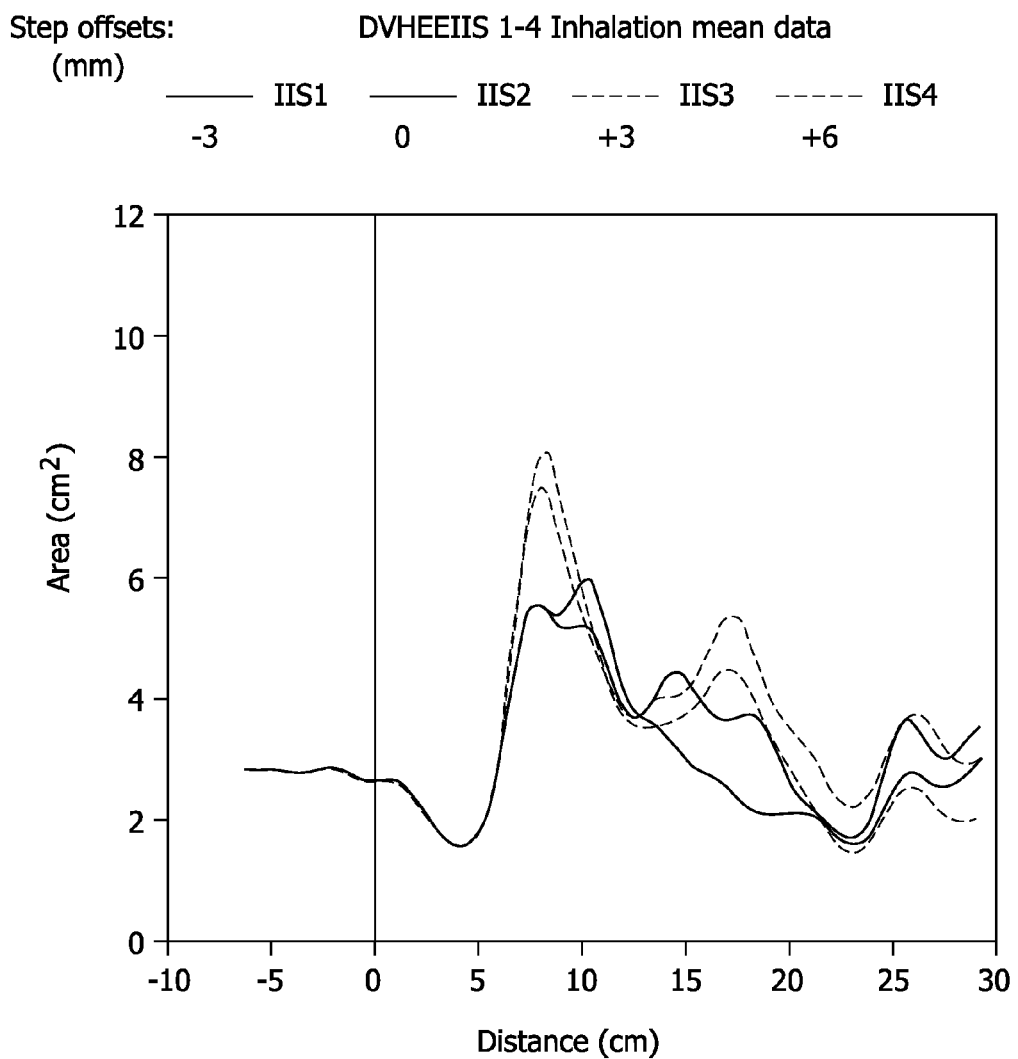
FIG. 10 shows four pharyngograms of four apparatuses with the same small cross section and with differing step offsets for a patient who suffers from sleep apnea.

FIG. 10 show four curves representing four different step offsets for apparatuses with 161 mm² cross section for patient 4 who suffers from sleep apnea. For the apparatus with step offset of −3 mm, FIG. 10 shows a lack of peak in the area of hypopharynx. This absence of a peak indicates a collapse of hypopharynx. However, the peak corresponding to hypopharynx is present in curves corresponding to apparatuses with positive step offsets. This is a surprising and unexpected result. This observation is indicative, that the apparatus is especially useful for people who suffer from sleep apnea.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus configured to aid aerosol delivery to a user comprising;
   a body, the body comprising:
      a proximal end comprising a medicament outlet;
      a distal end opposite the proximal end; a longitudinal axis
   a mouthpiece disposed at the proximal end, the mouthpiece being configured to be engaged within a mouth of the user in an as-used position of the apparatus, the mouthpiece comprising:
      a first side;
      a second side opposite the first side;
      a first stop disposed on the first side of the mouthpiece, the first stop having a facial-facing surface forming a vertical plane bisecting the device, configured to face in a patient distal-to-proximal direction when in use and perpendicular to a longitudinal axis of the body and being configured to engage a facial surface of one or more maxillary incisors of the user when the mouthpiece is engaged within the mouth of the user in the as-used position; and a second stop disposed on the second side of the mouthpiece opposite the first side, the second stop having a lingual-facing surface forming a second vertical plane bisecting the device, configured to face in a patient proximal-to-distal direction when in use and perpendicular to the longitudinal axis of the body and being configured to engage a lingual surface of one or more mandibular incisors of the user when the mouthpiece is engaged within the mouth of the user in the as-used position;

a tubular passageway communicating between the proximal end and the distal end, the passageway disposed along the longitudinal axis of the body forming a flow path to facilitate breathing by the user while the apparatus is in the as-used position; and wherein the first stop and the second stop are disposed and arranged on the mouthpiece and between the medicament outlet and the distal end of the body and on opposite sides of the passageway such that a lower mandible of the user is advanced toward the distal end of the body and is advanced relative to the one or more maxillary incisors along the longitudinal axis of the body when the apparatus is in the as-used position.

2. The apparatus of claim 1, wherein the first stop is offset along the longitudinal axis of the mouthpiece from the second stop and wherein the second stop is configured to extend the lower mandible toward the distal end by 1 to 6 mm from the first stop when the apparatus is in the as-used position.

3. The apparatus of claim 1, wherein the first stop is offset along the longitudinal axis of the mouthpiece from the second stop and wherein the second stop is configured to extend the lower mandible toward the distal end by 3 to 6 mm from the first stop when the apparatus is in the as-used position.

4. The apparatus of claim 1, wherein the distal end comprises an inlet port.

5. The apparatus of claim 4, wherein the inlet port is adapted to attach to an inhaled pharmaceutical aerosol delivery device.

6. The apparatus of claim 4, wherein the inlet port is adapted to attach to an inhaler.

7. An apparatus to aid aerosol delivery to a user comprising:

a body, the body having a first side and a second side opposite the first side, the body having a medicament outlet end, a longitudinal axis and a distal end opposite the medicament outlet end, the body comprising a bore through the apparatus from the distal end to the medicament outlet end along a longitudinal axis to facilitate breathing by the user while the apparatus is held within a mouth of the user in an as-used position of the apparatus;

a first stop on the first side of the apparatus, the first stop being disposed distally of the medicament outlet end and having a facial-facing surface forming a vertical plane bisecting the device, configured to face in a patient distal-to-proximal direction when in use and perpendicular to the longitudinal axis of the body and configured to engage a facial surface of one or more maxillary incisors of the user and a second stop on a second side of the apparatus, the second side being opposite the first side, forming a second vertical plane bisecting the device, configured to face in a patient proximal-to-distal direction when in use, the second stop being disposed distally of the medicament outlet end and configured to engage a lingual surface of one or more mandibular incisors of the user in the as-used position of the apparatus, wherein the relative position of the first stop and the second stop is such that upon insertion of the body into the user's mouth in the as-used position of the apparatus, a lower mandible of the user is advanced toward the distal end and relative to the one or more maxillary incisors along the longitudinal axis of the body.

8. The apparatus of claim 7, wherein a mandibular advancement opens an upper airway of the user.

9. A mouthpiece comprising:

a body, the body having a first side and a second side opposite the first side, the body having a medicament outlet end, a longitudinal axis and a distal end opposite the medicament outlet end, the body forming a tubular flow path therethrough along a longitudinal axis to facilitate breathing by a user while the mouthpiece is installed within a mouth of the user comprising an as-used position of the mouthpiece;

a first stop disposed on the first side, the first stop being disposed distally of the medicament outlet end and having a facial-facing surface forming a vertical plane bisecting the device, configured to face in a patient distal-to-proximal direction when in use and perpendicular to a longitudinal axis of the body and configured to engage a facial surface of one or more maxillary incisors of the user in the as-used position;

a second stop disposed on the second side, the second stop being disposed distally of the medicament outlet end and having a lingual-facing surface forming a second vertical plane bisecting the device, configured to face in a patient proximal-to-distal direction when in use and perpendicular to the longitudinal axis of the body and configured to engage a lingual surface of one or more mandibular incisors of the user when the mouthpiece is in the as-used position, wherein the relative positions of the first stop and the second stop are offset along the longitudinal axis of the mouthpiece and are positioned such that the first stop is nearer to the medicament outlet end than the second stop to advance a lower mandible of the user toward the distal end and relative to the one or more maxillary incisors along the longitudinal axis of the mouthpiece when the mouthpiece is in the as-used position.

10. The mouthpiece of claim 9, wherein the mouthpiece is further attached to an inhaled pharmaceutical aerosol delivery device.

11. The mouthpiece of claim 10, wherein the inhaled pharmaceutical aerosol delivery device is a nebulizer.

12. The mouthpiece of claim 10, wherein the inhaled pharmaceutical aerosol delivery device is an inhaler.

13. The mouthpiece of claim 12, wherein the inhaler is a metered dose inhaler.

14. The mouthpiece of claim 12, wherein the inhaler is a dry powder inhaler.

15. A method of aiding aerosol delivery to a user, the method comprising;

advancing a lower mandible of the user with a mandibular advancement apparatus, the mandibular advancement apparatus comprising a body, the body having a first side and a second side opposite the first side, the body having a medicament outlet end, a longitudinal axis a distal end opposite the medicament outlet end, the body having a first stop disposed distally of the medicament outlet end and having a facial-facing surface forming a vertical plane bisecting the device, configured to face in a patient distal-to-proximal direction when in use and perpendicular to the longitudinal axis of the body and configured to engage a facial surface of one or more maxillary incisors of the user and a second stop disposed distally of the medicament outlet end and having a lingual-facing surface forming a second vertical plane bisecting the device, configured to face in a patient proximal-to-distal direction when in use and perpendicular to the longitudinal axis of the body and configured to engage a lingual surface of one or more mandibular incisors of the user, the advancing of the lower mandible being toward the distal end along a longitudinal axis of the mandibular advancement apparatus such that the lingual surface of the one or more mandibular incisors is advanced along the longitudinal axis relative to the facial surface of the one or more maxillary incisors.

16. The method of claim 15, further comprising forming a bore through the body along the longitudinal axis to facilitate breathing by the user while the apparatus is held within the mouth of the user.

17. The method of claim 16, further comprising; introducing inhaled pharmaceutical aerosol through the bore of the body to the user.

18. The method of claim 16, further comprising, engaging the first stop of the mandibular advancement apparatus with a facial surface of one or more maxillary incisors of the user, the first stop disposed on the first side of the mandibular advancement apparatus, engaging the second stop of the mandibular advancement apparatus with a lingual surface of one or more mandibular incisors of the user, the second stop disposed on the second side of the mandibular advancement apparatus opposite the first side, and installing the mandibular advancement apparatus in a mouth of the user in an as used position of the mandibular advancement apparatus, such that the relative position of the first stop is nearer to the medicament outlet of the apparatus than the second stop.

19. An inhaled pharmaceutical aerosol delivery device comprising a mouthpiece, wherein the mouthpiece comprises:
an inlet;
a first stop disposed on a first side;
a second stop disposed on a second side opposite the first side;
a medicament-outlet end opposite the inlet; a longitudinal axis, the inlet and medicament outlet end connected by a tubular passageway extending therebetween;
wherein:
the first stop is disposed along a longitudinal axis of the device distally of the medicament outlet end and nearer to the medicament outlet end than the second stop, a first stop having a facial-facing surface forming a vertical plane bisecting the device, configured to face in a patient distal-to-proximal direction when in use and perpendicular to the longitudinal axis of the body and being configured to engage a facial surface of one or more maxillary incisors of the user in an as-used position of the device installed in a mouth of a user;
the second stop is disposed on the second side along the longitudinal axis of the device distally of the medicament outlet end and nearer to the inlet than the first stop, the second stop having a lingual-facing surface forming a second vertical plane bisecting the device, configured to face in a patient proximal-to-distal direction when in use and perpendicular to the longitudinal axis of the body and being configured to engage a lingual surface of one or more mandibular incisors of the user when the mouthpiece is in the as-used position;
wherein the relative positions of the first stop and the second stop are configured to advance a lower mandible of a user away from the medicament outlet end and relative to the one or more maxillary incisors along the longitudinal axis of the device when the mouthpiece is installed in the mouth of the user in the as-used position.

20. A metered dose inhaler comprising a mouthpiece, wherein the mouthpiece comprises:
an inlet;
a first stop on a first side;
a second stop on a second side opposite the first side;
a medicament-outlet end opposite the inlet; a longitudinal axis, the inlet and medicament outlet end connected by a tubular passageway extending therebetween; and
wherein:
the first stop is disposed on the first side to face toward the medicament outlet end and on an inlet side of the medicament outlet end;
the second stop is disposed on the second side to face away from the medicament outlet end and on an inlet side of the medicament outlet end;
the first stop having a facial-facing surface forming a vertical plane bisecting the device, configured to face in a patient distal-to-proximal direction when in use and perpendicular to the longitudinal axis of the body and being configured to engage a facial surface of one or more maxillary incisors of a user in an as-used position of the mouthpiece installed within a mouth of the user;
the second stop having a lingual-facing surface forming a second vertical plane bisecting the device, configured to face in a patient proximal-to-distal direction when in use and perpendicular to the longitudinal axis of the body and being configured to engage a lingual surface of one or more mandibular incisors of the user in the as-used position; and
the facial-facing surface of the first stop is disposed nearer to the medicament outlet end of the mouthpiece than the lingual-facing surface of the second stop, such that a lower mandible of the user is advanced away from the medicament outlet end and relative to the one or more maxillary incisors along a longitudinal axis of the mouthpiece when the mouthpiece is in the as-used position.

21. A metered dose inhaler actuator comprising a mouthpiece, wherein the mouthpiece comprises:
an inlet;
a first stop on a first side;
a second stop on a second side, the second side being opposite the first side;
a medicament-outlet end opposite the inlet; a longitudinal axis, the inlet and medicament outlet end connected by a tubular passageway extending therebetween; and
wherein:
the first stop is disposed on the first side to face toward the medicament outlet end and on an inlet side of the medicament outlet end;
the second stop is disposed on the second side to face away from the medicament outlet end and on an inlet side of the medicament outlet end;
the first stop having a facial-facing surface forming a vertical plane bisecting the device, configured to face in a patient distal-to-proximal direction when in use and perpendicular to a longitudinal axis of the body and being configured to engage a facial surface of one or more maxillary incisors of a user in an as-used position of the mouthpiece installed within a mouth of the user;

the second stop having a lingual-facing surface forming a second vertical plane bisecting the device, configured to face in a patient proximal-to-distal direction when in use and perpendicular to the longitudinal axis of the body and being configured to engage a lingual surface of one or more mandibular incisors of the user in the as-used position of the mouthpiece; and the first stop is disposed nearer to the medicament outlet end of the mouthpiece than the second stop, such that a lower mandible of the user is advanced away from the medicament outlet end and relative to the one or more maxillary incisors along a longitudinal axis of the mouthpiece when the mouthpiece is in the as-used position.

22. A dry powder inhaler comprising a mouthpiece, wherein the mouthpiece comprises:

an inlet;

a first stop on a first side;

a second stop on a second side opposite the first side;

a medicament-outlet end opposite the inlet; a longitudinal axis, the inlet and medicament outlet end connected by a tubular passageway extending therebetween;

wherein:

the first stop is disposed on the first side to face toward the medicament outlet end and on an inlet side of the medicament outlet end;

the second stop is disposed on the second side to face away from the medicament outlet end and on an inlet side of the medicament outlet end;

the first stop having a facial-facing surface forming a vertical plane bisecting the device, configured to face in a patient distal-to-proximal direction when in use and perpendicular to a longitudinal axis of the body and is configured to engage a facial surface of one or more maxillary incisors of the user in an as-used position of the mouthpiece installed within a mouth of the user;

the second stop having a lingual-facing surface forming a second vertical plane bisecting the device, configured to face in a patient proximal-to-distal direction when in use and perpendicular to the longitudinal axis of the body and being configured to engage a lingual surface of one or more mandibular incisors of the user in the as-used position;

the first stop is disposed nearer to the medicament outlet end of the mouthpiece than the second stop, such that a lower mandible of the user is advanced away from the medicament outlet end and relative to the one or more maxillary incisors along a longitudinal axis of the mouthpiece when the mouthpiece is in the as-used position.

23. An apparatus comprising:

an inlet port configured to receive an aerosol;

a mouthpiece configured to deliver such an aerosol to a user, the mouthpiece comprising a first stop having a facial-facing surface forming a vertical plane bisecting the device, configured to face in a patient distal-to-proximal direction when in use and perpendicular to a longitudinal axis of the body and configured to engage a facial surface of one or more maxillary incisors of the user in an as-used position of the mouthpiece installed within a mouth of the user and a second stop having a lingual-facing surface forming a second vertical plane bisecting the device, configured to face in a patient proximal-to-distal direction when in use and perpendicular to the longitudinal axis of the body and configured to engage a lingual surface of one or more mandibular incisors of the user in the as-used position, wherein, in the as-used position, a medicament outlet end of the mouthpiece is positioned on a lingual side of the one or more mandibular incisors and the one or more maxillary incisors; and a hollow body having a longitudinal axis disposed between the inlet port and the mouthpiece and extending therebetween, the hollow body configured to facilitate fluid communication of an aerosol from the inlet port to the mouthpiece;

wherein the mouthpiece includes an offset configuration of the first stop and second stop to impart a selected amount of mandibular advancement of the user's lower mandible relative to the user's maxilla and along a longitudinal axis of the mouthpiece during aerosol delivery;

wherein the mouthpiece has a cross-sectional area associated therewith, wherein the cross-sectional area is defined by a vertical component and a horizontal component, and wherein the vertical component defines the amount of vertical opening of the user's mouth during aerosol delivery, and wherein at least one of the offset, the vertical component, or a combination of the offset and vertical component are configured to provide a predetermined deposition of such an aerosol within the user's lungs.

* * * * *